(12) United States Patent
Barklis

(10) Patent No.: US 8,003,674 B2
(45) Date of Patent: Aug. 23, 2011

(54) FLAVIVIRUS INHIBITION BY SULTAMS AND RELATED COMPOUNDS

(75) Inventor: Eric Barklis, Lake Oswego, OR (US)

(73) Assignee: Oregon Health & Science University, Portland, OR (US)

( * ) Notice: Subject to any disclaimer, the term of this patent is extended or adjusted under 35 U.S.C. 154(b) by 204 days.

(21) Appl. No.: 12/279,831

(22) PCT Filed: Mar. 15, 2007

(86) PCT No.: PCT/US2007/006573
§ 371 (c)(1),
(2), (4) Date: Aug. 18, 2008

(87) PCT Pub. No.: WO2007/109105
PCT Pub. Date: Sep. 27, 2007

(65) Prior Publication Data
US 2010/0234434 A1    Sep. 16, 2010

Related U.S. Application Data

(60) Provisional application No. 60/783,353, filed on Mar. 16, 2006.

(51) Int. Cl.
*A61K 31/41* (2006.01)
(52) U.S. Cl. .................................. 514/360; 514/359
(58) Field of Classification Search .................. 514/360, 514/359
See application file for complete search history.

(56) References Cited

U.S. PATENT DOCUMENTS
6,258,831 B1    7/2001    Camden
2006/0025416 A1    2/2006    Phadke et al.

FOREIGN PATENT DOCUMENTS
WO    WO 2006/060774 A2    6/2006

OTHER PUBLICATIONS

Paula "New Drug target for hepatitis C and other Flaviviridae viruses," Infectious Disorders-Drug Targets, 2009, vol. 9, pp. 133-147.*
Buckwood et al. "Bovine viral diarrhea virus as a surrogate model of hepatitis C virus for the evaluation of antiviral agents," Antiviral Research, 2003, vol. 60 pp. 1-15.*
Linden and Goerdeler, "Reaktion von Iminodithiazolen mit Sulfenen zu S-Fliedrigen Sultamen," *Tetrahedron Letters* 20:1729-1732, 1977.
Barklis et al., "Sultam Thiourea Inhibition of West Nile Virus," *Antimicrob. Agents Chemother.* 51:2642-2645, 2007.

* cited by examiner

*Primary Examiner* — Shengjun Wang
(74) *Attorney, Agent, or Firm* — Klarquist Sparkman, LLP

(57) ABSTRACT

Disclosed herein are compounds, compositions and methods for treating or ameliorating flavivirus infections. This is particularly important because the present disclosure provides methods for treating flavivirus infections for which there is no effective vaccine.

13 Claims, 2 Drawing Sheets

FLAVIVIRUS INHIBITION BY SULTAMS AND RELATED COMPOUNDS

CROSS REFERENCE TO RELATED APPLICATION

This is the U.S. National Stage of Application No. PCT/US2007/006573, filed Mar. 15, 2007, which was published in English under PCT Article 21(2), which claims the benefit of U.S. Provisional Application No. 60/783,353, filed Mar. 16, 2006, which is incorporated herein by reference in its entirety.

ACKNOWLEDGMENT OF GOVERNMENT SUPPORT

This invention was made with government support under grant number R21 AI-056248 awarded by The National Institute of Allergy and Infectious Diseases of the National Institutes of Health. The government has certain rights in this invention.

FIELD

This disclosure concerns pharmaceutical chemistry, particularly methods for treating or ameliorating flavivirus infections using sultams and related compounds. Also disclosed are pharmaceutical compositions and methods for using such compositions to treat flavivirus infections.

BACKGROUND

Members of the Flaviviridae family that infect humans frequently cause severe morbidity and mortality, and epidemics of flaviviruses continue to be a major public health concern worldwide. Over half of the at least 70 distinct virus species of the genus Flavivirus are associated with human disease, and in all, more than two billion people are at risk of being infected with members of the genus. The medically important flaviviruses include yellow fever (YF) virus (predominantly in Africa, Latin and South America); Japanese encephalitis (JE) virus (predominantly in Asia and Australia); West Nile (WN) virus (predominantly in Africa, Central Europe, and most recently in North America); tick-borne encephalitis (TBE) complex viruses (predominantly in temperate regions worldwide); and the four serotypes of dengue viruses (DEN-1, -2, -3, and -4) (predominantly in tropical and subtropical regions of the world) (Lindenbach & Rice, *Flaviviridae: the viruses and their replication*. In *Fields Virology*, 4$^{th}$ ed., Knipe and Howley. Eds., Philadelphia, Lippincott Williams & Wilkins, pp. 991-1041, 2001; Burke & Monath, Flaviviruses. In *Fields Virology*, 4$^{th}$ ed., Knipe and Howley. Eds., Philadelphia, Lippincott Williams & Wilkins, pp. 1043-1125, 2001; Kuno et al., *J. Virol.* 1998, 72, 73-83, 1998; Solomon & Mallewa, *J. Infect.* 42:104-15, 2001).

West Nile Virus (WNV) outbreaks in particular have increased markedly in frequency and severity. Since first appearing in New York City in 1999, the virus has spread to the entire continental United States with outbreaks occurring each subsequent summer.

Another member of the Flaviviridae family causes hepatitis, which affects nearly 750,000 Americans each year, and out of those, more than 150,000 are infected with the hepatitis C virus (HCV). HCV is most closely related pestiviruses, which include hog cholera virus and bovine viral diarrhea virus (BVDV).

SUMMARY OF THE DISCLOSURE

Disclosed herein are compounds, compositions and methods for treating flavivirus infections. In one aspect, the compounds can be represented by the formula wherein X is —S—, —S(O)—, —SO$_2$—, —N—; —CH$_2$—, —N(R$^3$)—, —C(O)— or —O—,
Y is —S—, —N(R$^4$)—, —C(R$^5$)(R$^6$)—, or —O—;
Z is S, N or O;
J is N or C(R$^7$);
A is —N(R$^8$)(R$^9$), —OR$^8$ or —CR$^9$R$^{10}$R$^{11}$;
G is N or CH;
R$^1$ is selected from H, lower alkyl, aralkyl, aryl, halogen and halo alkyl;
R$^2$ is selected from lower alkyl, aralkyl, aryl;
R$^3$, R$^4$, R$^5$, R$^6$ and R$^7$ independently are selected from H, lower alkyl, heteroalkyl, heterocyclyl, aralkyl and aryl
R$^8$ and R$^9$ independently are selected from lower alkyl, heteroalkyl, heterocyclyl, aralkyl and aryl; and
R$^{10}$ and R$^{11}$ independently are selected from H, lower alkyl, heteroalkyl, heterocyclyl, aralkyl and aryl and including hydrates and pharmaceutically acceptable prodrugs and salts thereof. Moreover, all chiral, diastereomeric and geometric isomeric forms of the disclosed formulas are intended.

The foregoing and other objects, features, and advantages of the disclosed compounds, compositions and methods will become more apparent from the following detailed description, which proceeds with reference to the accompanying figure.

DETAILED DESCRIPTION

Figure 1:
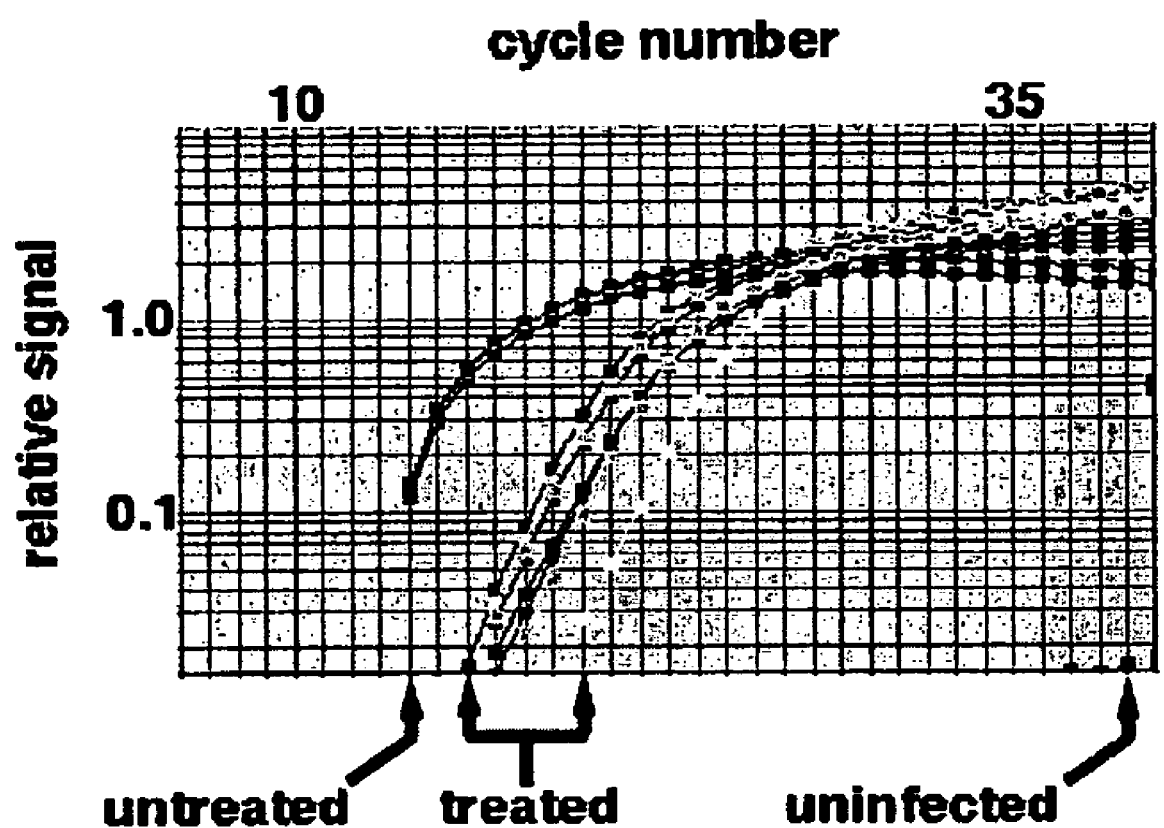
FIG. 1 is a graph demonstrating that WNV RNA levels are lower in infected cells treated with TYT-1.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance can but need not occur, and that the description includes instances where said event or circumstance occurs and instances where it does not.

"Derivative" refers to a compound or portion of a compound that is derived from or is theoretically derivable from a parent compound.

The term "subject" includes both human and veterinary subjects.

The term "treating a disease" refers to inhibiting the full development of and/or reversing progression or development of a disease or condition, for example, in a subject who is infected with a virus or at risk for viral infection (for example, a flavivirus infection, such as West Nile Virus). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology or decreasing its severity.

The term "alkyl group" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "alkenyl group" refers to a hydrocarbon group of 2 to 24 carbon atoms and structural formula containing at least one carbon-carbon double bond.

The term "alkynyl group" refers to a hydrocarbon group of 2 to 24 carbon atoms and a structural formula containing at least one carbon-carbon triple bond.

The terms "halogenated alkyl group" or "haloalkyl group" refer to an alkyl group as defined above with one or more hydrogen atoms present on these groups substituted with a halogen (F, Cl, Br, I).

The term "cycloalkyl group" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "aliphatic group" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "aryl group" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted. The term "alkyl amino" refers to alkyl groups as defined above where at least one hydrogen atom is replaced with an amino group.

The term "hydroxyl group" is represented by the formula —OH. The term "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above.

The term "hydroxyalkyl group" refers to an alkyl group that has at least one hydrogen atom substituted with a hydroxyl group. The term "alkoxyalkyl group" is defined as an alkyl group that has at least one hydrogen atom substituted with an alkoxy group described above. Where applicable, the alkyl portion of a hydroxyalkyl group or an alkoxyalkyl group can have aryl, aralkyl, halogen, hydroxy and/or alkoxy substituents.

The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

The term "aralkyl" refers to an aryl group having an alkyl group, as defined above, attached to the aryl group. An example of an aralkyl group is a benzyl group.

Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "pharmaceutically acceptable salt or prodrug" is used throughout the specification to describe any pharmaceutically acceptable form (e.g., ester, phosphate ester, salt of an ester or a related group) of a sultam compound, which, upon administration to a subject, provides or produces an active compound. Pharmaceutically acceptable salts include those derived from pharmaceutically acceptable inorganic or organic bases and acids. In particular, suitable salts include those derived from alkali metals such as potassium and sodium, alkaline earth metals such as calcium and magnesium, among numerous other acids well known in the pharmaceutical art.

The disclosed compounds also encompass salts including, if several salt-forming groups are present, mixed salts and/or internal salts. The salts are generally pharmaceutically-acceptable salts that are nontoxic or substantially nontoxic to a subject. Examples of salt-forming acidic groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl) amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Particular compounds possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Pharmaceutically acceptable prodrugs refer to compounds that are metabolized, for example, hydrolyzed or oxidized, in the subject to form an antiviral compound of the present disclosure. Typical examples of prodrugs include compounds that have one or more biologically labile protecting groups in or otherwise blocking a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against a flavivirus, or are metabolized to a compound that exhibits such activity.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a hydroxy, amino, or sulfhydryl group functionalized with any group that is cleaved to yield the corresponding hydroxyl, free amino, or free sulfhydryl group, respectively. Examples of prodrugs include, without limitation, compounds having a hydroxy, amino and/or sulfhydryl group acylated with an acetate, formate, and/or benzoate group.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the presently preferred compounds.

I. ANTIVIRAL COMPOUNDS

In general the antiviral compounds used in the methods disclosed herein can be represented by the formula

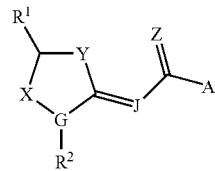

wherein X is —S—, —S(O)—, —SO$_2$—, —N—; —CH$_2$—, —N(R$^3$)—, —C(O)— or —O—,

Y is —S—, —N(R$^4$)—, —C(R$^5$)(R$^6$)—, or —O—;

Z is S, N or O;

J is N or C(R$^7$);

A is —N(R$^8$)(R$^9$), —OR$^8$ or —CR$^9$R$^{10}$R$^{11}$;

G is N or CH;

R$^1$ is selected from H, lower alkyl, aralkyl, aryl, halogen and halo alkyl;

R$^2$ is selected from lower alkyl, aralkyl, aryl;

R$^3$, R$^4$, R$^5$, R$^6$ and R$^7$ independently are selected from H, lower alkyl, heteroalkyl, heterocyclyl, aralkyl and aryl R$^8$ and R$^9$ independently are selected from lower alkyl, heteroalkyl, heterocyclyl, aralkyl and aryl; and R$^{10}$ and R$^{11}$ independently are selected from H, lower alkyl, heteroalkyl, heterocyclyl, aralkyl and aryl.

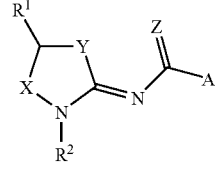

wherein X is —S—, —S(O)—, —SO$_2$—, —N— or —O—;

Y is —S—, —N— or —O—;

Z is S, N or O;

A is —N(R$^8$)(R$^9$) or —OR$^8$;

R$^1$ is selected from H, lower alkyl, aralkyl, aryl, halogen and halo alkyl;

$R^2$ is selected from lower alkyl, aralkyl, aryl; and $R^8$ and $R^9$ independently are selected from lower alkyl, heteroalkyl, heterocyclyl, aralkyl and aryl.

With reference to the formulas presented above, in certain embodiments, A represents a sterically bulky group. Such groups are known to those of skill in the art, and examples of such groups include, without limitation, those wherein $R^8$, $R^9$, $R^{10}$ and/or $R^{11}$ represent a branched alkyl group or substituted phenyl. Particular examples of such groups include, without limitation, isopropyl, t-butyl and mesityl.

Exemplary embodiments of antiviral compounds include those wherein $R^2$ represents

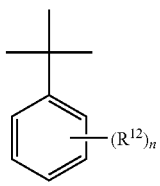

In such compounds $R^{12}$ is independently selected for each n from aryl, halogen, haloalkyl, lower alkyl, alkoxy, hydroxy, and n is an integer of 0-5. As is understood by those of ordinary skill in the art when n is less than 5, the ortho, meta and para carbon atoms are bonded to H. For example, certain compounds having n=0 can be represented by the formula

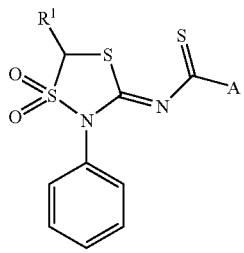

Certain examples of antiviral compounds for use in the present methods, have the formula

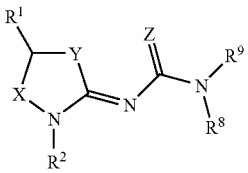

wherein X is —S—, —S(O)—, —SO$_2$—, —N— or —O—;

Y is —S—, —N— or —O—;

Z is S, N or O;

$R^1$ is selected from H, lower alkyl, aralkyl, aryl, halogen and halo alkyl;

$R^2$ is selected from lower alkyl, aralkyl, aryl; and $R^8$ and $R^9$ independently are selected from lower alkyl, heteroalkyl, heterocyclyl, aralkyl and aryl.

Particular examples of such compounds include a thiocarbamate or thiourethane moiety as represented by the formula

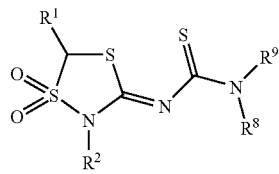

wherein $R^1$; $R^2$; $R^8$ and $R^9$ are as set forth above.

Still other examples of antiviral compounds useful for treating flavivirus infections include those having the formula

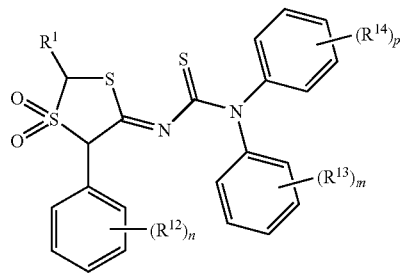

wherein $R^1$ is selected from H, lower alkyl and aryl; $R^{12}$, $R^{13}$ and $R^{14}$, are for each n, m and p, independently selected from lower alkyl, halogen and haloalkyl; and n, m and p independently are from 0-5, such as 0, 1, two or 3.

Additional examples of antiviral compounds disclosed herein include those of the formula

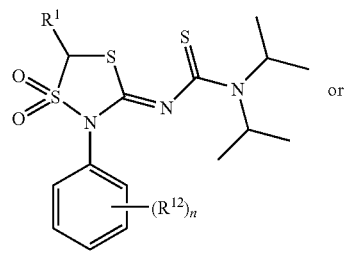

or

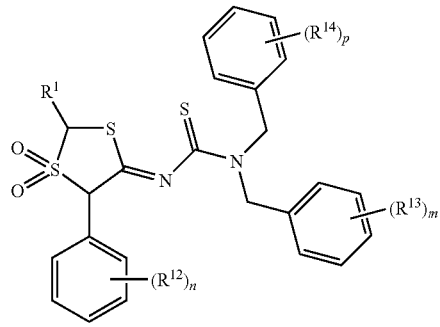

Particular examples of antiviral compounds disclosed herein include those described in Table 1.

TABLE 1

| Compound | Appearance | ¹H NMR (ppm)/solvent | IR cm⁻¹ CHCl₃ |
|---|---|---|---|
| *(structure: 3-phenyl-1,2,3-dithiazolidine 2,2-dioxide with N,N-dimethylthiourea)* | bright yellow needles (mp = 150° C. (decomp.)) | 5.05 s (2) (methylene); 7.27-7.50 (phenyl) | 1555 s 1480 m 1350 s 1140 s |
| *(structure: 3-phenyl-1,2,3-dithiazolidine 2,2-dioxide with N,N-diethylthiourea)* | bright yellow needles (mp = 198° C. (decomp.)) | 0.70 t (3); 1.08 t (3); 3.17 q (2); 3.72 q (2); 5.07 s (2) (methylene); 7.29-7.75 (5)/DMSO | 1560 s 1495 s 1350 s 1140 s |
| *(structure: 3,5-dimethyl-1,2,3-dithiazolidine 2,2-dioxide with N,N-diisopropylthiourea)* | yellow (mp = 208° C. (decomp.)) | 1.23 d (6); 1.47 d (6); 1.72 d (3) 3.33 s (3); 3.88 (1); 4.30 q (1); 5.58 (1)/CDCl₃ | 1550 s 1475 s 1340 s 1140 s |
| *(structure: 3-methyl-1,2,3-dithiazolidine 2,2-dioxide with N,N-diisopropylthiourea)* | bright yellow needles (mp = 132° C.) | 1.25 d (6) 1.47 d (6) 3.31 s (3) 3.91 (1) 4.21 s (2) 5.53 (1)/CDCl₃ | 1550 s 1475 s 1340 s 1140 s |
| *(structure: 3-methyl-5-phenyl-1,2,3-dithiazolidine 2,2-dioxide with N,N-diisopropylthiourea)* | yellow flakes (mp = 187° C. (decomp.)) | 1.27 d (6) 1.47 d (3) 1.54 d (3) 3.40 s (3) 3.95 (1) 5.48 s (1) 5.60 (1) ca. 7.5 (5)/CDCl₃ | 1540 s 1475 s 1335 s 1150 s |
| *(structure: 3-benzyl-1,2,3-dithiazolidine 2,2-dioxide with N,N-diisopropylthiourea)* | bright yellow needles (mp = 129° C.) | 1.10 d (6) 1.28 d (6) 3.90 (1) 4.26 s (2) 5.09 (1) 5.09 s (2) 7.32 s/CDCl₃ | 1540 s 1475 s 1340 s 1130 s |

TABLE 1-continued

| Compound | Appearance | ¹H NMR (ppm)/solvent | IR cm⁻¹ CHCl₃ |
|---|---|---|---|
| [structure] | bright yellow (mp = 124° C.) | 1.07 d (3) 1.10 d (3) 1.27 d (6) 3.90 (1) 4.40 q (1) 5.06 (1) 5.06 s (2) 7.39 s /CDCl₃ | 1545 m 1475 s 1340 s 1140 s |
| [structure] | colorless needles (mp = 221° C. (decomp.)) | 4.43 s (2) 5.02 s (2) 5.15 s (2) 6.69-7.58 (15)/ DMSO | 1560 s 1475 s 1350 s 1145 s |
| [structure] | bright yellow needles (mp = 203° C. (decomp.)) | 5.14 s (2); 6.40-7.60 (15)/ DMSO | 1550 s 1485 s 1360 s 1140 s |
| [structure] | bright yellow needles (mp = 168° C. (decomp.)) | 1.20 t (3) 4.31 q (2); 5.22 s (2); 7.26-7.72 (5)/ DMSO | 1525 s 1360 s 1140 s |
| [structure] | violet needles (mp = 119° C. (decomp.)) | 2.08 s (6); 2.20 (3); 4.38 s (2); 6.75 s (2); 7.26-7.72 (5)/ CDCl₃ | 1480 s (br.) 1355 s 1140 s |

II. COMPOSITIONS AND METHODS OF TREATMENT

Another aspect of the disclosure includes pharmaceutical compositions prepared for administration to a subject and which include a therapeutically effective amount of one or more of the currently disclosed compounds. Disclosed also are methods for administering the disclosed compounds and compositions. The therapeutically effective amount of a disclosed compound will depend on the route of administration, the type of mammal that is the subject and the physical characteristics of the subject being treated. Specific factors that can be taken into account include disease severity and stage, weight, diet and concurrent medications. For example, in one aspect one or more of the disclosed compounds can be administered as a prophylactic. In another aspect the disclosed compounds can be used to treat a subject infected with a flavivirus. The relationship of these factors to determining a therapeutically effective amount of the disclosed compounds is understood by those of ordinary skill in the art.

The active compound can be administered as any salt or prodrug that upon administration to the recipient is capable of providing directly or indirectly the parent compound, or that exhibits activity itself. Nonlimiting examples are the pharmaceutically acceptable salts, which are alternatively referred to as "physiologically acceptable salts." Further, the modifications can affect the biological activity of the compound, in some cases increasing the activity over the parent compound. This can be readily assessed by preparing the salt or prodrug and testing its antiviral activity according to the methods described herein, or other methods known to those skilled in the art.

In one embodiment of the invention, a method of treatment or prophylaxis of a subject infected with, or at risk for infection with, a flavivirus is provided that includes administering an antivirally effective amount of a compound of the present disclosure to the subject, optionally in combination or alternation or sequentially with another antiviral agent. In another embodiment, the use of a disclosed compound for the treatment of a subject infected with a flavivirus, and particularly hepatitis C is provided. In a particular embodiment, a method of treatment of a subject infected with West Nile virus is provided. Additional methods include those employing a compound of the disclosure for the treatment of a subject infected with Japanese encephalitis virus or Dengue virus. In yet another embodiment, the use of a compound of the invention in the manufacture of a medicament for the treatment of a subject infected with a flavivirus is provided.

The dosages given will depend on absorption, inactivation and excretion rates of the drug(s) as well as other factors known to those of skill in the art. It is to be noted that dosage values may also vary with the severity of the condition to be alleviated. It is to be further understood that for any particular subject, specific dosage regimens and schedules may be adjusted over time according to the individual need and the professional judgment of the person administering or supervising the administration of the compositions. In some embodiments, an anti-flavivirus compound that exhibits an $IC_{50}$ of less than about 20 µM, such as 10-15 µM, or typically less than 1-5 µM, is desirable.

The therapeutically effective amount or antivirally effective amount of the compound or compounds administered can vary depending upon the desired effects and the factors noted above. In particular examples dosages are administered that achieve target tissue concentrations that have been found to be effective in vitro. Typically, dosages will be between about 0.01 mg/kg and 100 mg/kg of the subject's body weight, and more typically between about 0.05 mg/kg and 10 mg/kg, such as from about 0.2 to about 5 mg/kg of the subject's body weight. An exemplary dose of the compound for flavivirus will be in the range from about 1 to 50 mg/kg, typically 1 to 20 mg/kg, of body weight per day, more generally 0.1 to about 100 mg per kilogram body weight of the recipient per day. The antivirally effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit dosage form, including but not limited to a dosage unit containing 7 to 3000 mg, typically 70 to 1400 mg of active ingredient per unit dosage form. An oral dosage of 50-1000 mg is usually convenient.

In one embodiment, an antiviral compound may be administered to achieve peak plasma concentrations of the active compound of from about 0.2 to 70 µM, typically about 1 to 10 µM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. Dosage values may also vary with the severity of the condition to be alleviated. Further, for any particular subject, specific dosage regimens should be adjusted over time according to the individual need and the professional judgment of the person administering or supervising the administration of the compositions, and concentration ranges set forth herein are exemplary only and are not intended to limit the scope or practice of the claimed composition.

Flaviviruses included within the scope of the disclosed method are discussed generally in Fields Virology, Editors: Fields, N., Knipe, D. M. and Howley, P. M.; Lippincott-Raven Publishers, Philadelphia, Pa.; Chapter 31 (1996). Specific flaviviruses include, without limitation: Absettarov; Alfuy; Apoi; Aroa; Bagaza; Banzi; Bououi; Bussuquara; Cacipacore; Carey Island; Dakar bat; Dengue serotypes 1, 2, 3 and 4; Edge Hill; Entebbe bat; Gadgets Gully; Hanzalova; Hepatitis C; Hypr; Ilheus; Israel turkey meningoencephalitis; Japanese encephalitis; Jugra; Jutiapa; Kadam; Karshi; Kedougou; Kokoera; Koutango; Kumlinge; Kunjin; Kyasanur Forest disease; Langat; Louping ill; Meaban; Modoc; Montana myotis leukoencephalitis; Murray valley encephalitis; Naranjal; Negishi; Ntaya; Omsk hemorrhagic fever; Phnom-Penh bat; Powassan; Rio Bravo; Rocio; Royal Farm; Russian spring-summer encephalitis; Saboya; St. Louis encephalitis; Sal Vieja; San Perlita; Saumarez Reef; Sepik; Sokuluk; Spondweni; Stratford; Temusu; Tyuleniy; Uganda S, Usutu, Wesselsbron; West Nile; Yaounde; Yellow fever; and Zika.

Pestiviruses that can be treated as disclosed herein also are discussed generally in Fields Virology. Specific pestiviruses include, without limitation: bovine viral diarrhea virus ("VDV"); classical swine fever virus ("CSFV") also known as hog cholera virus); and border disease virus ("DV").

Drug-resistant variants of flaviviruses may emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound to which the virus is susceptible. Alternatively, the pharmacokinetics, biodistribution or other parameter of the drug can be altered by such combination or alternation therapy. Combination therapy can be used rather than alternation therapy because it causes multiple simultaneous stresses on the virus.

In principle any effective viral treatment can be used in combination or alternation with the compounds described in this specification. Nonlimiting examples include: an interferon and/or ribavirin (see, for example, Battaglia, A. M. et al., *Ann. Pharmacother.* 34:487-494, 2000; and Berenguer, M. et al. *Antivir. Ther.* 3(Suppl. 3):125-136, 1998)). Additional antiviral agents suitable for combination therapy include substrate-based NS3 protease inhibitors (see, for example, Attwood et al., Antiviral peptide derivatives, WO 98/22496, 1998; Tung et al. Inhibitors of serine proteases, particularly hepatitis C virus NS3 protease, WO 98/17679), including alphaketoamides and hydrazinoureas, and inhibitors that terminate in an electrophile such as a boronic acid or phosphonate (see, for example, Llinas-Brunet et al., Hepatitis C inhibitor peptide analogues, WO 99/07734).

Non-substrate-based inhibitors such as 2,4,6-trihydroxy-3-nitro-benzamide derivatives (see, for example, Sudo K. et al., Biochemical and Biophysical Research Communications: 1997, 238, 643-647; Sudo K. et al. Antiviral Chemistry and Chemotherapy: 1998, 9, 186), including RD3-4082 and RD3-4078, also can be used in combination with the presently disclosed antiviral agents.

Additional suitable antiviral agents for use in combination with the disclosed antiviral agents include, without limitation, thiazolidine derivatives, for example, that inhibition in a relevant assay (see, for example, Sudo K. et al., Antiviral Research, 1996, 32, 9-18), especially compound RD-1-6250, possessing a fused cinnamoyl moiety substituted with a long alkyl chain, RD4 6205 and RD4 6193. Similarly, thiazolidines and benzanilides can be employed, for example, as identified in Kakiuchi N. et al. *J. EBS Letters* 421, 217-220; Takeshita N. et al. *Analytical Biochemistry*, 1997, 247, 242-246.

Selective NS3 inhibitors, for example, based on the macromolecule elgin c, isolated from leech (see, for example, Qasim M. A. et al., *Biochemistry*, 1997, 36, 1598-1607) also are useful in combination with the disclosed compounds, as are helicase inhibitors (see, for example, U.S. Pat. No. 5,633, 358 to Diana G. D. et al.

Polymerase inhibitors such as nucleotide analogues, for example, gliotoxin (see, for example, Ferrari R. et al., *Journal of Virology*, 1999, 73, 1649-1654) can also be used. Inhibitors of IRES-dependent translation also can be used in combination with the disclosed compounds (see, for example, Ikeda N et al., Agent for the prevention and treatment of hepatitis C, Japanese Patent Pub. JP-08268890; Kai Y. et al. Prevention and treatment of viral diseases, Japanese Patent Pub. JP-10101591). Nuclease-resistant ribozymes also can be used in combination therapy with the disclosed antiviral compounds (see, for example, Maccjak, D. J. et al., *Hepatology*, 1999, 30, abstract 995).

The compounds and compositions disclosed herein may be administered by various routes, including orally, topically, transdermally, parenterally, via inhalation or spray and may be administered in dosage unit formulations containing conventional non-toxic pharmaceutically acceptable carriers, adjuvants and vehicles.

Typically, oral administration or administration intravenously, such as via injection, is preferred. However the particular mode of administration employed may be influenced by the particular disease, condition (and species) of patient, toxicity of compound and other factors as will be recognized by a person of ordinary skill in the art.

Pharmaceutical compositions for administration to a subject can include carriers, thickeners, diluents, buffers, preservatives, surface active agents and the like in addition to the active molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

III. EXAMPLES

The foregoing disclosure is further explained by the following non-limiting examples.

Example 1

Synthesis of Inhibitor Compounds

This example describes a general method for preparing sultam compounds for use in the disclosed methods. The method is illustrated by the following scheme:

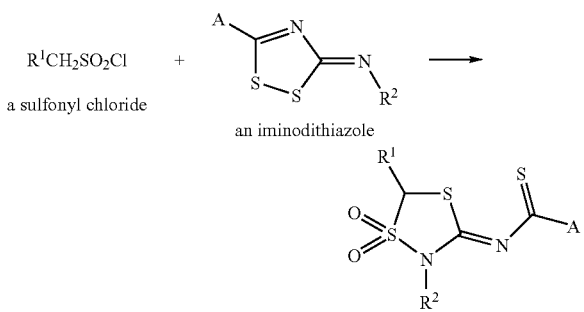

This scheme typically employs one equivalent of the iminodithiazole and an excess of a tertiary amine base, for example triethylamine, in a dichloromethane solvent. 1.5 equivalents of the sulfonyl chloride is dissolved in dichloromethane and slowly added dropwise to the iminodithiazole solution at 0° C. Afterwards the organic phase is washed several times with water, dried and the sultam compound crystallized. This one-step protocol is described in by Linden, H., and Goerdeler, J. Ring opening cycloadditions. Part 5. Reaction of iminodithiazoles with sulfenes in 5-membered sultams. *Tetrahedron Lett.* 1977, 20, 1729-1732, which is incorporated herein by reference.

A variety of iminodithiazoles can be prepared as is known to those of skill in the art. For example, one general synthesis follows the scheme:

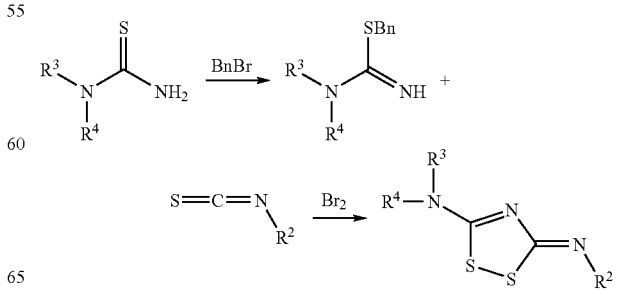

An alternative general iminodithiazole synthesis proceeds according to the following scheme

[Reaction scheme: $R^3R^4N-C(=S)-Cl$ → (KNCS) → $[R^3R^4N-C(=S)-NCS]$ → ($R^2NH_2$) → $R^3R^4N-C(=S)-NH-C(=S)-NHR^2$ → ($I_2$) → iminodithiazole product with substituents $R^3$, $R^4$, $R^2$]

Representative iminodithiazole compounds that can be used to prepare antiviral compounds disclosed herein are described by Dixit, S., and Verma, V. *Ind. J. Chem.* 1963, 1, 487-489. Spurlock, L., and Newllis, P. The reactions of carbamoyl chlorides with thiocyanate ion. *J. Org. Chem.* 33, 2073-2076. Oliver, J., Chang, S., Brown, R., and Borkovec, A. (1971). *J. Med. Chem.* 1968, 14, 772; and Oliver, J., and DeMilo, A. *J. Org. Chem.* 1974, 39, 2225-2228. Each of these references is incorporated herein by reference.

Example 2

Evaluation of Inhibitor Activity

This example describes an assay used to evaluate inhibitor antiviral activity.

Inhibitor screening, virus yield reduction, and cytotoxicity assays all employed Vero cells and media containing 2% FCS. Compound libraries were assayed for WNV antiviral activity by screening for protection of infected Vero cells from WNV cytopathic effects (CPE). To do so, $10^4$ Vero cells in 96 well plate wells were pretreated with a final concentration of 10 μg/mL drug in a total volume of 1 μL DMSO, infected with WNV at a multiplicity of infection (MOI) of 0.2, and screened for protection from CPE for 3-5 d post-infection (PI). Virus yield reduction assays were modified from previous protocols (Hirsch, A., Medigeshi, G., Meyers, H., DeFilippis, V., Fruh, K., Briese, T., Lipkin, W. I., and Nelson, J. (2005). The Src family kinase c-Yes is required for maturation of West Nile virus particles. *J. Virol.* 79, 11943-11951.). Briefly, $10^4$ Vero cells in 96 well plate wells were treated with compound dilutions in 1 μL DMSO, and infected with WNV at an MOI of 1-3. At 20-24 h PI, virus-containing media samples were titered by limiting dilution on fresh Vero cells. After 5 d, media were removed, and surviving cells were stained with 0.0375% crystal violet in ethanol. For cytotoxicity assays, $10^4$ Vero cells per 96 well plate well were treated with compound dilutions, grown for 48 h, and subjected to colorimetric assays for dehydrogenase levels in metabolically active cells using MTS (3-[4,5-dimethylthiazol-2-yl]-5-[3-carboxymethyoxy phenyl]-2-[4-sulfophenyl]-2H-tetrazolium]; Promega) substrate. MTS cytotoxicity assay results were confirmed microscopically by scoring for Trypan Blue (0.2%) exclusion.

Several antiviral sultams were evaluated in using these methods. The results, including $CC_{50}$ and $EC_{50}$ values for WNV and JEV, were determined by MTS cytotoxicity assays and virus yield reduction assays and are recorded in Table 2.

TABLE 2

Antiviral and cytotoxic activities of exemplary compounds.

| Compound | WNV $EC_{50}$ | JEV $EC_{50}$ | $CC_{50}$ |
| --- | --- | --- | --- |
| TYT-1 | 0.7 μM | 7 μM | >70 μM |
| TYT-2 | 30 μM | 30 μM | 90 μM |
| TYT-3 | 80 μM | 8 μM | >80 μM |
| TYT-4 | 22 μM | 65 μM | 65 μM |

With reference to Table 2, the compounds assayed included sultams TYT-1, N'-(1,1-dioxido-2-phenyl-1,4,2-dithiazolidin-3-ylidene)-N,N-diphenylthiourea; TYT-2, (2,5-dimethyl-1,1-dioxido-1,4,2-dithiazolidin-3-ylidene)bis(1-methylethyl)thiourea; TYT-3, [1,1-dioxido-2-(phenylmethyl)-1,4,2-dithiazolidin-3-ylidene]bis(1-methylethyl)-thiourea; TYT-4, (1,1-dioxido-2-phenyl-1,4,2-dithiazolidin-3-ylidene)-bis(phenylmethyl)-thiourea. With continued reference to Table 2, cytotoxic concentrations ($CC_{50}$) are significantly higher than the observed $EC_{50}$ values for each of the sultam antivirals, with the exception of TYT-4. Indeed, 50% cytotoxicity was not obtained for TYT-1 and TYT-3 with the highest drug concentrations employed.

In this assay TYT-1 (N'-(1,1-dioxido-2-phenyl-1,4,2-dithiazolidin-3-ylidene)-N,N-diphenyl thiourea; MW 439.6) reduced viral titers by at least 100-fold at 1 μg/ml concentrations. In repeated tests, TYT-1 consistently reduced WNV titers 100- to 10,000-fold. TYT-1 has the structure:

TYT-1

[Chemical structure of TYT-1: a 1,1-dioxido-1,4,2-dithiazolidine ring with phenyl substituent, connected via =N to C(=S)N(phenyl)₂]

In contrast with the activity of TYT-1 ribavirin at <100 μM, interferon alpha (1000 IU/ml), and a variety of 20 μM antisense oligonucleotide derivatives aimed at the capsid AUG, the polymerase AUG, and 5' and 3' cyclization sequences failed to protect cells from a WNV (0.2 MOI) challenge (Brinton, M. (2002). The molecular biology of West Nile virus. *Ann. Rev. Microbiol.* 56, 371-402). 100 μM ribavirin reduced WNV titers 10-fold, relative to the 100-10,000 fold observed for much lower concentrations of TYT-1.

Example 3

Inhibitor Effect on E Protein Expression

This example demonstrates that TYT-1 blocks WNV replication. E protein expression was assayed by immunofluorescence and immunoblotting. Immunofluorescent and immunoblot detection of WNV E employed a commercially available anti-E monoclonal antibody (Chemicon Mab 8150). For immunofluorescence, Vero cells in DMEM, plus penicillin, streptomycin, and 2% FCS were mock-treated with DMSO, or treated with 10 μg/mL of inhibitor compound in DMSO, and infected with WNV at an MOI of 3. At 24 h PI, cells were processed for immunofluorescent detection of WNV E using a standard protocol at room temperature (Arvidson, B., Seeds, J., Webb, M., Finlay, L., and Barklis, E. (2003). Analysis of the retrovirus capsid interdomain linker region. *Virology* 308, 166-177). Briefly, washed cells were fixed 20 min in 3.7% formaldehyde in phosphate-buffered saline (PBS; 9.5 mM sodium potassium phosphate [pH 7.4], 137 mM NaCl, 2.7 mM KCl), washed, permeabilized 10 min in 0.2% Triton X-100 in PBS, washed, incubated 1 h with primary antibody diluted in DMEM plus 10% heat inactivated FCS (DMEM+FCS), washed, incubated 1 h with 1:1000 diluted Alexafluor594-conjugated goat antimouse secondary antibody (Molecular Probes; Invitrogen) in DMEM+FCS, washed, and mounted with PBS in 50% glycerol. Images were collected electronically on a Zeiss fluorescence microscope.

For immunoblot detection of WNV E Vero cells on 3 mm plates in 1 mL media were mock-treated with 5 µL DMSO or treated with 5 µL 1 mg/mL inhibitor compound in DMSO (final concentration 5 µg/mL inhibitor compound), and infected with WNV at an MOI of 5. At 18 h PI, media were removed, cells were collected in IPB (10 mM Tris-hydrochloride [pH 7.5], 150 mM NaCl, 1 mM ethylenediaminetetraacetic acid (EDTA), 0.1% sodium dodecyl sulfate [SDS], 0.5% sodium deoxycholate, 1% Triton X-100, 0.02% sodium azide), mixed with 1 volume of 2× sample buffer (12.5 mM Tris-hydrochloride [pH 6.8], 2% SDS, 20% glycerol, 0.25% bromphenol blue) plus 0.1 volume of β-mercaptoethanol (β-Me). Samples were frozen at −20° C., heated 5 min to 90° C. and subjected to SDS-polyacrylamide gel electrophoresis (SDS-PAGE). After electrophoresis and electroblotting onto nitrocellulose filters, WNV E proteins were detected using a dilution of Mab 8150 as the primary antibody, an alkaline phosphatase-conjugated goat antimouse IgG secondary antibody (Promega), and a BCIP (5-bromo-4-chloro-3-indolyl phosphate) plus NBT (nitroblue tetrazolium)-mediated color reaction for visualization.

Nearly all of the mock-pretreated cells gave a strong perinuclear staining of WNV E. In contrast, very few cells treated with inhibitor compound, particularly TYT-1, expressed high levels of WNV E. To demonstrate that the reduced number of stained cells was not due to a reduced number of cells on the slides, micrographs of TYT-1-treated and infected cells were taken at longer exposure times. A handful of E protein-positive cells was observed over the faint background staining of the majority of cells.

Immunoblotting was performed using a similar infection regime as in the immunofluorescence protocol. Pretreated or mock-treated Vero cells were infected at an MOI of 5, and lysed and processed for immunoblot detection of WNV E at 18 h PI. A faint low molecular weight, cross-reactive cellular protein is visible in uninfected and infected cells, which served as a convenient internal control for gel loading and blotting. The WNV envelope protein was detected as a band at approximately 55 kDa in cells treated with DMSO, or with ineffective candidate inhibitors. Importantly, cells treated with TYT-1 gave essentially no E protein signal, corroborating the immunofluorescence results.

Example 4

Inhibitor Effect on Viral RNA

As demonstrated in Example 3, TYT-1 dramatically reduced WNV E protein expression levels in infected cells. This example demonstrates that the TYT-1 also reduces viral RNA levels. Cells were DMSO mock-treated or treated with 5 µg/ml TYT-1, and then mock-infected or infected with WNV NY99 at an MOI of 5. At 18 h PI, RNAs were isolated from cells and subjected to reverse transcription (RT) real-time PCR quantitation of WNV RNA following the protocol of Briese et al. (Briese, T., Glass, W., and Lipkin, W. I. (2000). Detection of West Nile virus sequences in cerebrospinal fluid. *Lancet* 355, 1614-1615). With reference to FIG. 1, RNA from uninfected cells gave essentially no WNV-specific real-time PCR signal, while quadruplicate samples from infected, mock-treated cells showed detectable signals by the fourteenth PCR cycle. Signal-to-cycle curves for TYT-1-treated cells were shifted to the right, demonstrating a clear reduction in WNV RNA levels. Indeed, while untreated cells at 18 h PI showed an average of 3255 WNV RNAs per cell, levels were 27 copies per cell for TYT-1-treated cells. Thus, inhibition of WNV NY99 replication by TYT-1 is accompanied by a reduction in viral protein and viral RNA expression levels.

Example 5

Inhibitor Toxicity Screening Assay

This example describes an assay used to screen inhibitors for undesired toxicity. TYT-1 was screened for toxicities using a colorimetric cell proliferation assay which employs MTS substrate to measure dehydrogenase activity in metabolically active cells (Barltrop, J. et al. (1991) 5-(3-carboxymethoxyphenyl)-2-(4,5-dimethyl thiazolyl)-3-(4-sulfophenyl)tetrazolium, inner salt (MTS) and related analogs of 3-(4,5-dimethyl thiazolyl)-2,5-diphenyltetrazolium bromide (mTT) reducing to purple water-soluble formazans as cell-viability indicators. *Bioorg. & Med. Chem. Lett.* 1, 611).

In this assay, subconfluent Vero cells were untreated, or treated 3 d with 10 µg/ml compound, and then subjected to MTS dehydrogenase assays, in which 490 nm absorbance values are proportional to cell viability signals. Results were plotted as the percentage of all treated compounds versus the percentage of the assay signal for untreated samples. Thus, nontoxic compounds give a signal approximately 100% that of the untreated signal. In this assay, the TYT-1 signal was 136% of untreated levels, demonstrating the relative lack of toxicity associated with this compound.

Example 6

Prophylactic Effect of Inhibitors

Figure 2A:
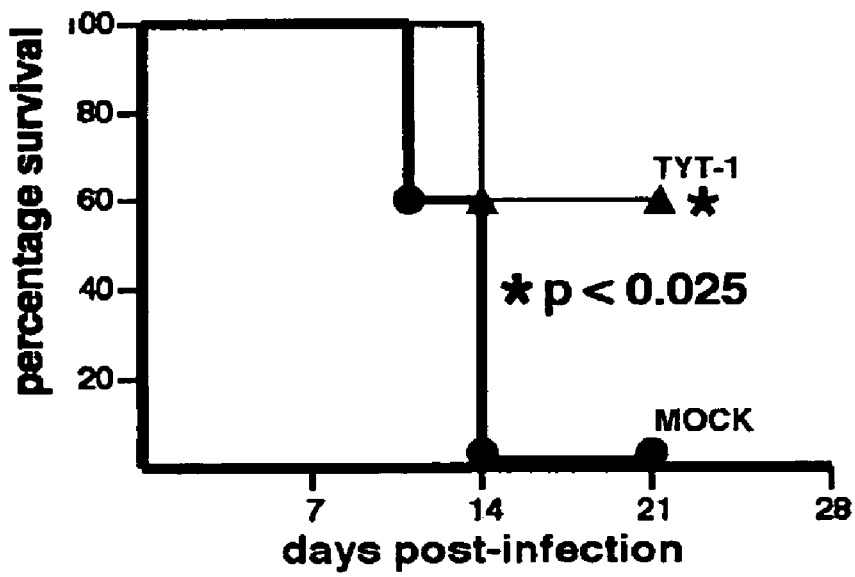
FIG. 2A is a chart illustrating the prophylactic effect of the disclosed compounds against WNV lethality.
Figure 2B:
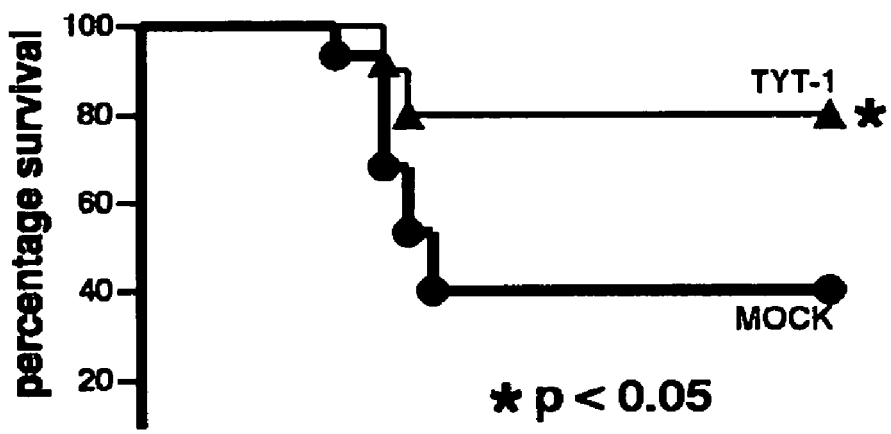
FIG. 2B is second chart illustrating the prophylactic effect of the disclosed compounds against WNV lethality.

This example describes the protective effect exerted by examples of the disclosed compounds against challenge with flaviviruses. In specific, TYT-1 was demonstrated to protect mice from infection with WNV. With reference to FIG. 2A, on day 0, two groups of five C57BL/6N mice each were injected subcutaneously with 400 plaque forming units (pfu) of West Nile virus (WNV; strain NY99). Four hours prior to virus infection, and at two and four days post-infection (PI), one set of mice was injected i.p. with 0.02 ml DMSO per mouse (mock), while the other set was injected with 10 mg/kg TYT-1 in 0.02 ml DMSO. Survival was tracked for 21 days PI, and results are plotted as overall percentage survival for each group, versus the number of days PI. At 21 days, all five DMSO mock-treated animals had succumbed, versus two out of five for the TYT-1-treated group. The Chi Squared probability that these results could occur randomly is p<0.025. With reference to FIG. 2B, two groups of C57BL/6N mice were infected on day 0 with WNV as described above. Prior to infection, the 15 mice in the mock group were injected subcutaneously with 0.025 ml of DMSO, while the 10 mice in the experimental group were injected with 10 mg/kg TYT-1 in DMSO. Mice subsequently were injected i.p. with DMSO or TYT-1 at days 2, 4, 6, 8; and survival was tracked as above. The Chi Squared probability that these results could occur randomly is p<0.05. The combined results of these two trial yielded a survival rate of 6/20 for mock treated mice and 11/15 for TYT-1 treated mice. These results demonstrate that TYT-1 treatment is protective against WNV-induced lethality with a Chi Squared probability of approximately p=0.01.

Example 7

Assaying Additional Inhibitors

This example describes the evaluation of additional inhibitors of flaviviruses. Exemplary compounds for evaluation by this method include, without limitation:

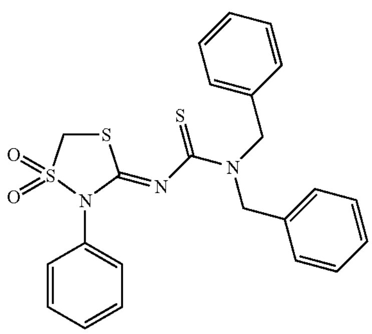

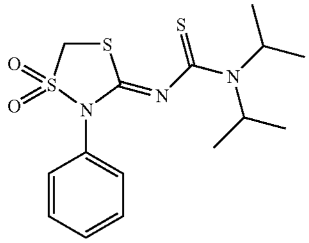

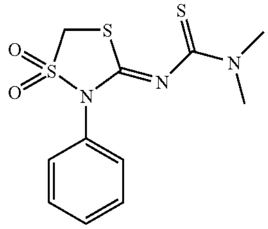

In general the method of Example 2 can be used to evaluate the efficacy of additional compounds against different flavivirus strains, and in different cell lines. Because large number of compounds will be tested, therefore a first screening assay can be performed. In this protocol wells in 96 well plates will be seeded with Vero cells, pretreated with 10 μg/ml compound, infected at an MOI of 0.2, and visually monitored for CPE and cell death at 2-5 d PI. Active compounds can be rescreened at 10 μg/ml and 1 μg/ml, and the most active inhibitor-virus strain combinations can be selected for closer analysis.

Further evaluation of the selected inhibitors will follow the approaches set forth in Examples 3 and 4. Specifically, virus titer reductions by inhibitors will be assayed by limiting dilution or plaque assay, and effects on viral protein and RNA levels at 18 h PI will be monitored by immunoblotting and real-time PCR. As an immunoblot protein level and sample loading control, immunoblots for originally blotted viral E or C proteins can be reblotted for detection of cellular actin levels. Similarly, parallel detection of cellular actin RNA or ribosomal protein L3 RNA levels can be used as reverse transcription real-time PCR controls (Peckham, I., Sobel, S., Comer, J., et al. (1989). Retrovirus activation in embryonal carcinoma cells by cellular promoters. *Genes and Devel.* 3, 2062-2071). Fifty percent inhibition of viral replication concentrations ($IC_{50}$) of compounds will be determined in Vero cells using two-fold dilution series of antiviral compounds, and assaying virus titers and vRNA levels. As noted above, selected inhibitors also can be tested in different cell lines by immunoblotting and/or viral RNA (vRNA) quantitation to evaluate possible cell type-specific effects on compound activities. We also will perform two indirect tests of inhibitor stabilities. For one test, compound dilutions will be incubated in media at 37° C. for 1-72 h prior to cell treatment, high MOI infection, and viral protein and RNA analysis. The second test will follow a similar regimen, except that the cells to be infected will be pretreated with compound dilutions. Comparison of results from these studies with derivative structures may help identify chemical features which have an impact on inhibitor stabilities and efficacies.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method for inhibiting flavivirus replication, comprising contacting a virus with a compound selected from the group consisting of N'-(1,1-dioxido-2-phenyl-1,4,2-dithiazolidin-3-ylidene)-N,N-diphenylthiourea (TYT-1); (2,5-dimethyl-1,1-dioxido-1,4,2-dithiazolidin-3-ylidene)bis(1-methylethyl)thiourea (TYT-2); [1,1-dioxido-2-(phenylmethyl)-1,4,2-dithiazolidin-3-ylidene]bis(1-methylethyl)-thiourea (TYT-3); (1,1-dioxido-2-phenyl-1,4,2-dithiazolidin-3-ylidene)-bis(phenylmethyl)-thiourea (TYT-4); and combinations thereof, wherein the virus is selected from West Nile virus and Japanese encephalitis virus.

2. The method of claim 1, wherein the compound comprises N'-(1,1-dioxido-2-phenyl-1,4,2-dithiazolidin-3-ylidene)-N,N-diphenylthiourea (TYT-1).

3. The method of claim 1, wherein the compound comprises (2,5-dimethyl-1,1-dioxido-1,4,2-dithiazolidin-3-ylidene)bis(1-methylethyl)thiourea (TYT-2).

4. The method of claim 1, wherein the compound comprises [1,1-dioxido-2-(phenylmethyl)-1,4,2-dithiazolidin-3-ylidene]bis(1-methylethyl)-thiourea (TYT-3).

5. The method of claim 1, wherein the compound comprises (1,1-dioxido-2-phenyl-1,4,2-dithiazolidin-3-ylidene)-bis(phenylmethyl)-thiourea (TYT-4).

6. A method of treating or ameliorating a viral infection in a subject, comprising identifying a subject infected with a virus; and administering to the subject an effective amount of a compound selected from the group consisting of N'-(1,1-dioxido-2-phenyl-1,4,2-dithiazolidin-3-ylidene)-N,N-diphenylthiourea (TYT-1); (2,5-dimethyl-1,1-dioxido-1,4,2-dithiazolidin-3-ylidene)bis(1-methylethyl)

thiourea (TYT-2); [1,1-dioxido-2-(phenylmethyl)-1,4,2-dithiazolidin-3-ylidene]bis(1-methylethyl)-thiourea (TYT-3); (1,1-dioxido-2-phenyl-1,4,2-dithiazolidin-3-ylidene)-bis(phenylmethyl)-thiourea (TYT-4); and combinations thereof, wherein the virus is selected from West Nile virus and Japanese encephalitis virus.

7. The method of claim 6, wherein administering comprises administering from about 0.1 to about 100 milligrams of the compound per kilogram of body weight per day.

8. The method of claim 6, wherein administering comprises administering from about 1 to about 20 milligrams of the compound per kilogram of body weight per day.

9. The method of claim 6, wherein the compound is administered in unit dosage form.

10. The method of claim 6, wherein the compound comprises N'-(1,1-dioxido-2-phenyl-1,4,2-dithiazolidin-3-ylidene)-N,N-diphenylthiourea (TYT-1).

11. The method of claim 6, wherein the compound comprises (2,5-dimethyl-1,1-dioxido-1,4,2-dithiazolidin-3-ylidene)bis(1-methylethyl)thiourea (TYT-2).

12. The method of claim 6, wherein the compound comprises [1,1-dioxido-2-(phenylmethyl)-1,4,2-dithiazolidin-3-ylidene]bis(1-methylethyl)-thiourea (TYT-3).

13. The method of claim 6, wherein the compound comprises (1,1-dioxido-2-phenyl-1,4,2-dithiazolidin-3-ylidene)-bis(phenylmethyl)-thiourea (TYT-4).

* * * * *

UNITED STATES PATENT AND TRADEMARK OFFICE
CERTIFICATE OF CORRECTION

PATENT NO.        : 8,003,674 B2
APPLICATION NO.   : 12/279831
DATED             : August 23, 2011
INVENTOR(S)       : Eric Barklis It is certified that error appears in the above-identified patent and that said Letters Patent is hereby corrected as shown below:

In the Specification:

Column 1, line 65, "related pestiviruses" should read --related to pestiviruses--

Column 2, line 47, "is second" should read --is a second--

Column 8, lines 52-63, the chemical structure

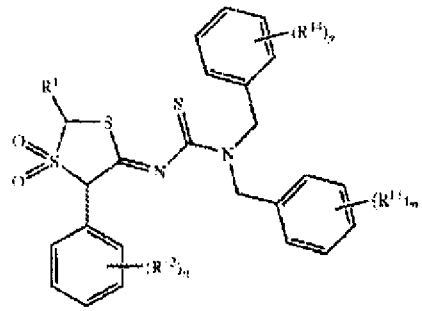 " should read -- 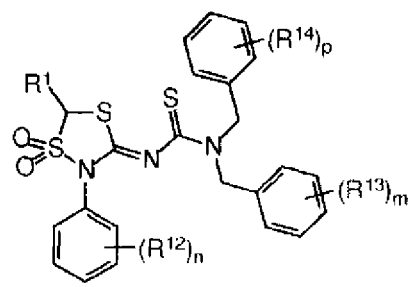 --

Column 9, in Table 1 (fourth listed compound), "1.47 d (6)" should read --1.48 d(6)--

Column 9, in Table 1 (sixth listed compound) should be reformatted to read:

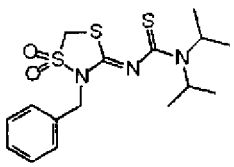

| | | |
|---|---|---|
| bright yellow needles (mp = 129 °C) | 1.10 d (6)<br>1.28 d (6)<br>3.90 (1)<br>4.26 s (2)<br>5.09 (1)<br>5.09 s (2)<br>7.32 s/CDCl$_3$ | 1540 s<br>1475 s<br>1340 s<br>1130 s |

Signed and Sealed this
First Day of May, 2012

David J. Kappos
*Director of the United States Patent and Trademark Office*

CERTIFICATE OF CORRECTION (continued)
U.S. Pat. No. 8,003,674 B2

Column 11, in Table 1 (second listed compound), "(2) 5.15 s (2)" should read --(2) 5.12 s (2)--

Column 14, lines 38-39, "also known as hog cholera virus)" should read --, also known as hog cholera virus--

Column 14, line 58, "1998))" should read --1998)--

Column 15, line 10, "that inhibition" should read --that show inhibition--

Column 15, lines 23-24, "5,633, 385 to Diana G. D. et al." should read --5,633,385 to Diana G. D. et al.).--

Column 16, line 42, "chloride is dissolved" should read --chloride are dissolved--

Column 16, line 46, "in by" should read --in--

Column 17, line 59, "dimethylthiazol-2yl)-5" should read --dimethylthiazol-2-yl-5--

Column 17, line 64, "evaluated in using" should read --evaluated using--

Column 18, lines 30-41, the chemical structure

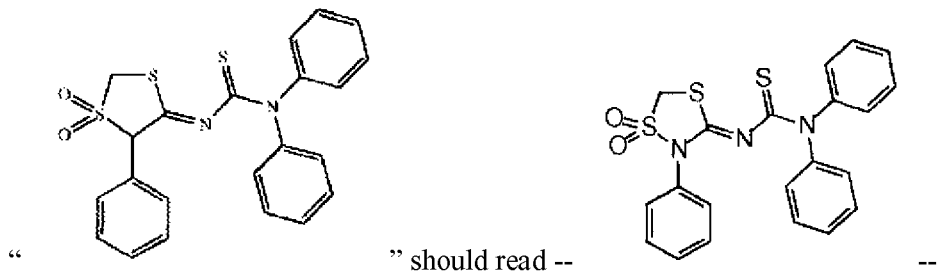

Column 21, line 3, "trial" should read --trials--

Column 21, line 57, "Because large" should read --Because a large--

Column 21, line 58, "therefore a first" should read --a first--